United States Patent [19]

Yost et al.

[11] Patent Number: 5,746,209
[45] Date of Patent: May 5, 1998

[54] METHOD OF AND APPARATUS FOR HISTOLOGICAL HUMAN TISSUE CHARACTERIZATION USING ULTRASOUND

[75] Inventors: William T. Yost, Newport News; John H. Cantrell, Yorktown, both of Va.; George A. Taler, Baltimore, Md.

[73] Assignee: The United States of America as represented by the Administrator of the National Aeronautics and Space Administration, Washington, D.C.

[21] Appl. No.: 592,833

[22] Filed: Jan. 26, 1996

[51] Int. Cl.⁶ ............................................. A61B 8/00
[52] U.S. Cl. ............................................. 128/661.03
[58] Field of Search .................. 128/660.01, 660.06, 128/660.07, 661.03, 660.02

[56] References Cited

U.S. PATENT DOCUMENTS

| | | | |
|---|---|---|---|
| 4,202,215 | 5/1980 | Meyer | 128/660.06 X |
| 4,385,634 | 5/1983 | Bowen | 128/660.01 X |
| 4,803,994 | 2/1989 | Burke | 128/660.06 |
| 4,817,015 | 3/1989 | Insana et al. | 364/507 |
| 4,858,124 | 8/1989 | Lizzi et al. | 364/413.01 |
| 4,982,339 | 1/1991 | Insana et al. | 128/660.01 X |
| 5,031,627 | 7/1991 | Yost et al. | 128/660.06 |
| 5,417,215 | 5/1995 | Evans et al. | 128/660.06 |
| 5,483,965 | 1/1996 | Wiener et al. | 128/661.03 |

OTHER PUBLICATIONS

Ophir et al., "Attenuation Estimation in Reflection: Progress and Prospects", UTS Imaging 6, 349–395 (1984).

*Primary Examiner*—Francis Jaworski
*Attorney, Agent, or Firm*—George F. Helfrich

[57] ABSTRACT

A method and apparatus for determining important histological characteristics of tissue, including a determination of the tissue's health. Electrical pulses are converted into meaningful numerical representations through the use of Fourier Transforms. These numerical representations are then used to determine important histological characteristics of tissue. This novel invention does not require rectification and thus provides for detailed information from the ultrasonic scan.

4 Claims, 5 Drawing Sheets

METHOD OF AND APPARATUS FOR HISTOLOGICAL HUMAN TISSUE CHARACTERIZATION USING ULTRASOUND

ORIGIN OF THE INVENTION

The invention described herein was jointly made by employees of the United States Government and an employee of the University of Maryland Medical School. It may be used by and for the Government for governmental purposes without the payment of any royalties thereon or therefor.

BACKGROUND OF THE INVENTION

1. Technical Field of the Invention

This invention relates to the medical classification of human tissue as healthy or unhealthy. More specifically, the invention uses ultrasound for determining histological characteristics of tissue by converting the return energy pulses into numerical terms, thus facilitating a quantitative analysis for medical diagnosis.

2. Discussion of the Related Art

Ultrasound has routinely been used in the medical profession to determine the shape, size and thickness of human tissue. Historically, this has been achieved through the detection of specular reflections from macroscopic tissue interfaces. Although this method allows for a general characterization of the tissue, it does not reveal its underlying health and structure. In order to obtain such a detailed analysis, reflections from the microscopic interfaces (scatterers) contained within the tissue must also be detected. An improved invention to detect these scatterers has yet to be discovered.

The prior art is able to determine general characteristics of tissue from its macroscopic interface reflections. This is commonly determined by transforming analog ultrasonic radio frequency data into a visual display. This technique requires the expertise of a skilled operator to interpret the display which does not include an accurate determination of the underlying pathology of the tissue.

Other prior art systems use Fourier Transforms to detect microscopic reflections; however, these systems do not allow for direct measurement of reflectance through self-calibration, and therefore are subject to calibration problems. These methods separate the components of an ultrasonic pulse into corresponding frequencies, using the Fourier Transform. This requires a reference plate to normalize the Fourier energy from the reflected tissue and thus the accuracy and range of available data is limited.

Similarly, the prior art taught by Sommer, Joynt, Carroll and Macovski ("Ultrasound characterization of abdominal tissues via digital analysis of backscattered wavefronts", Radiology, 141:811-7, 1981) uses a Fourier analysis to determine the mean spacing of scatterers in the liver and spleen. This method, however, does not provide for the determination of key variables that give ranges for specific tissues and their state of health.

U.S. Pat. No. 5,417,215 of Evans et al. provides a method of interpreting the microscopic interfaces which requires demodulating the return energy pulses by full-wave rectification to obtain the amplitude modulation of the pulses and computing the power spectrum by performing a Fast Fourier Transform on the rectified, digitized pulses. The requirement of rectification limits this method in providing information from the ultrasonic scan. It does not provide specific, well established physical parameters of the body tissue under investigation. It requires the comparison of Fourier energies or ratios, as well as, comparisons based on correlations.

It is, therefore, an objective of the invention to provide an improved ultrasound tissue characterization system for histological tissue classification.

It is a further objective of the invention to provide a system which does not require rectification, thereby allowing a more detailed analysis.

SUMMARY OF THE INVENTION

The present invention converts electrical pulses into meaningful numerical representations through the use of Fourier Transforms. This information can be used to determine important histological characteristics of tissue, including a determination of the tissue's health. This novel invention does not require rectification and thus provides for a much more detailed information from the ultrasonic scan.

DETAILED DESCRIPTION OF THE INVENTION

Figure 1:
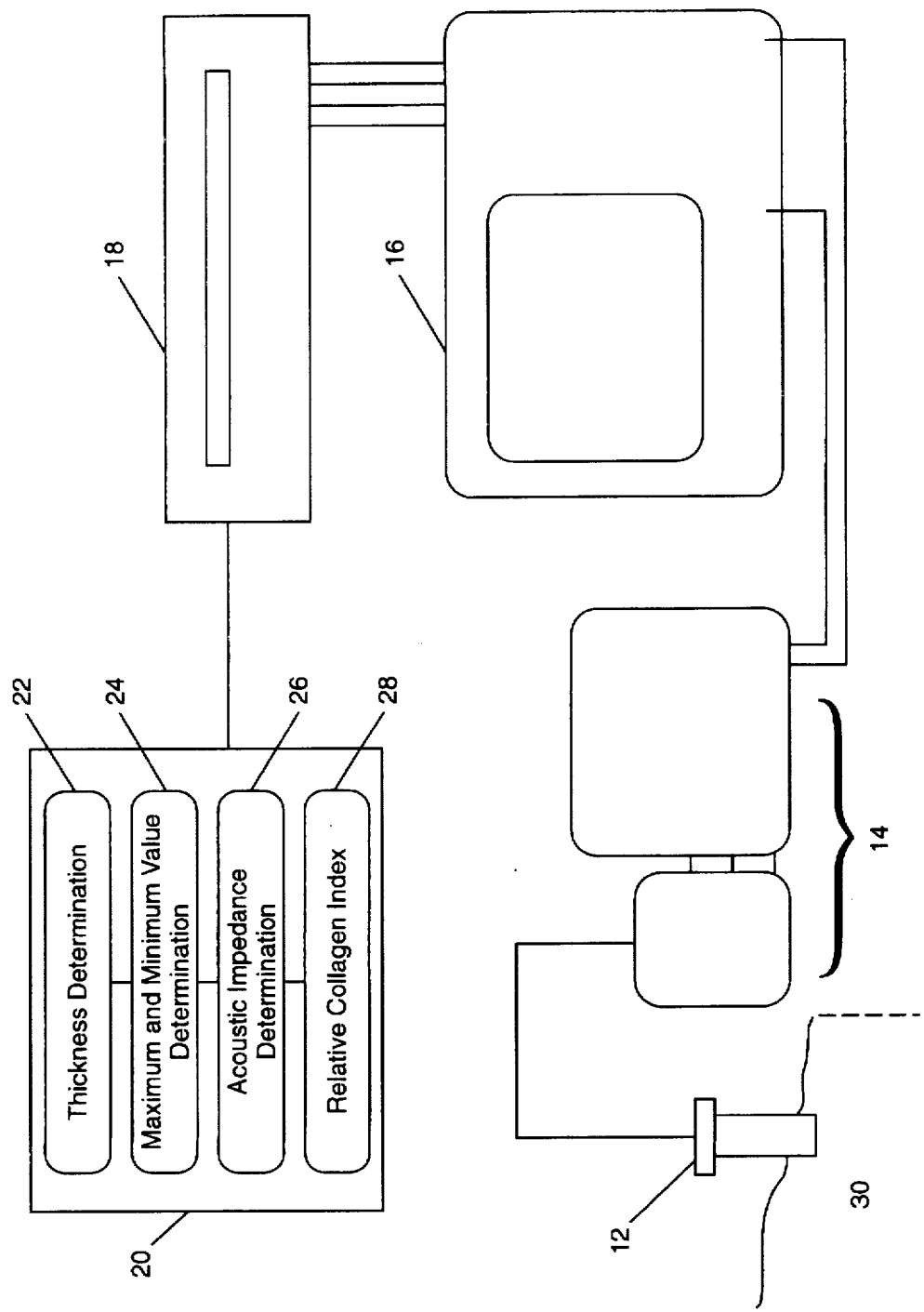
FIG. 1 is an equipment diagram for data taking.
Figure 2:
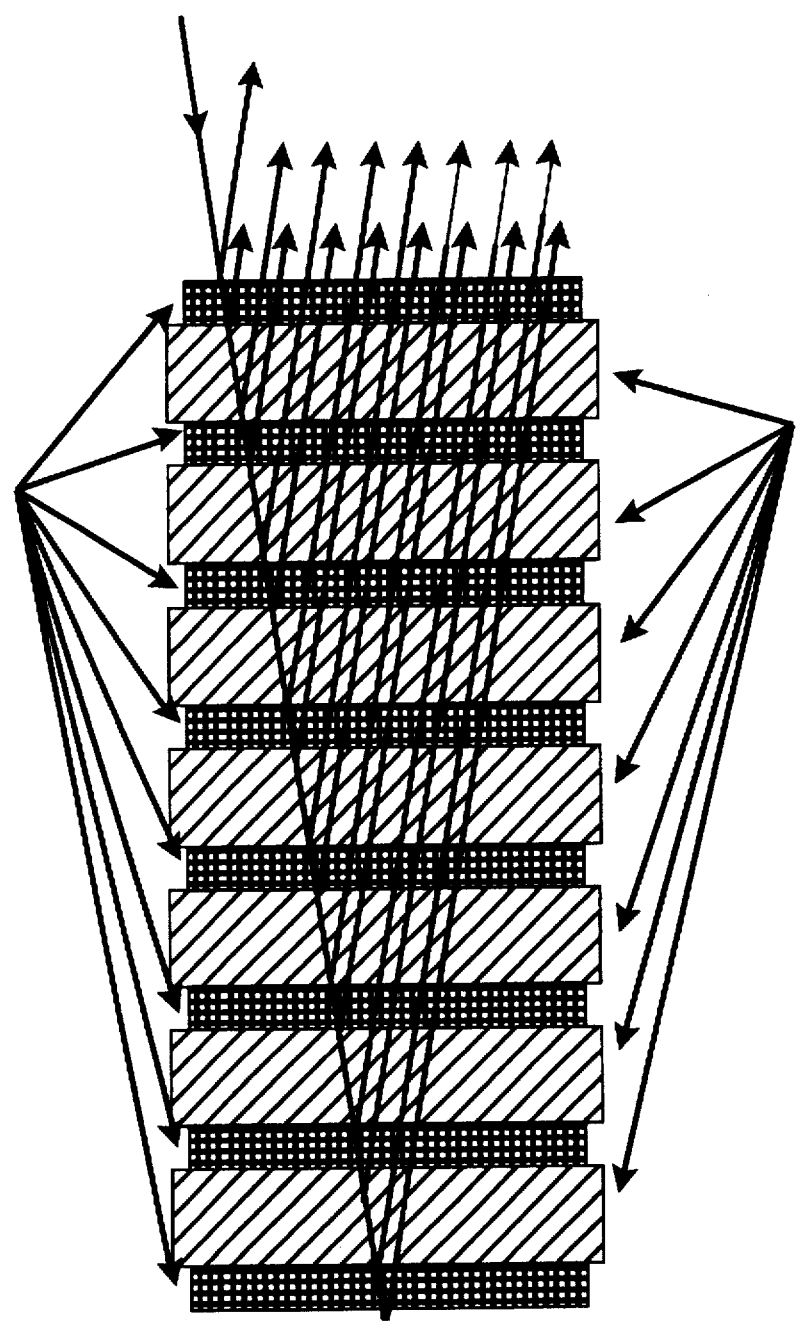
FIG. 2 is an illustration of an ultrasonic wave passing through an iterated structure constructed from two acoustically different tissue types.
Figure 3:
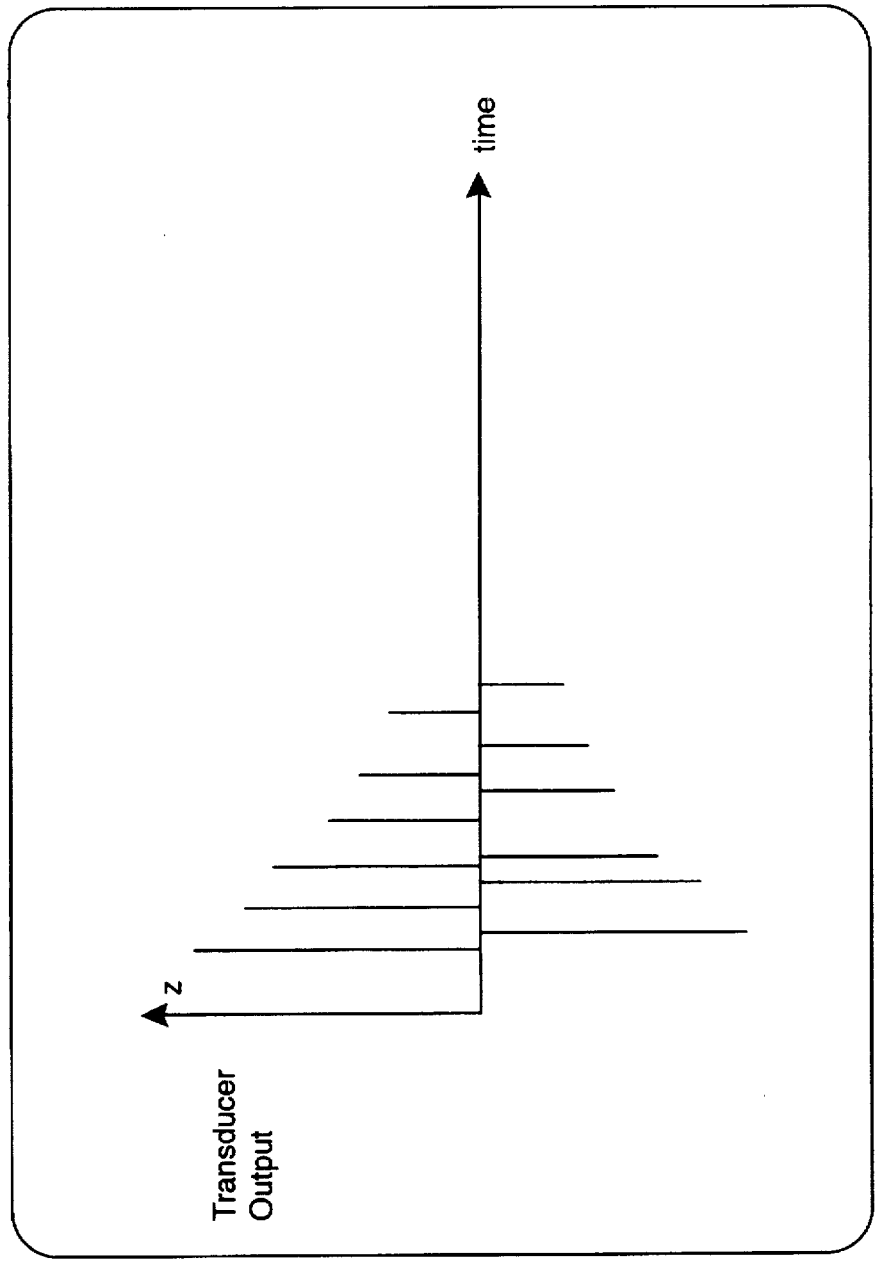
FIG. 3 is a typical ultrasonic echo pattern received from tissue reflections.
Figure 4:
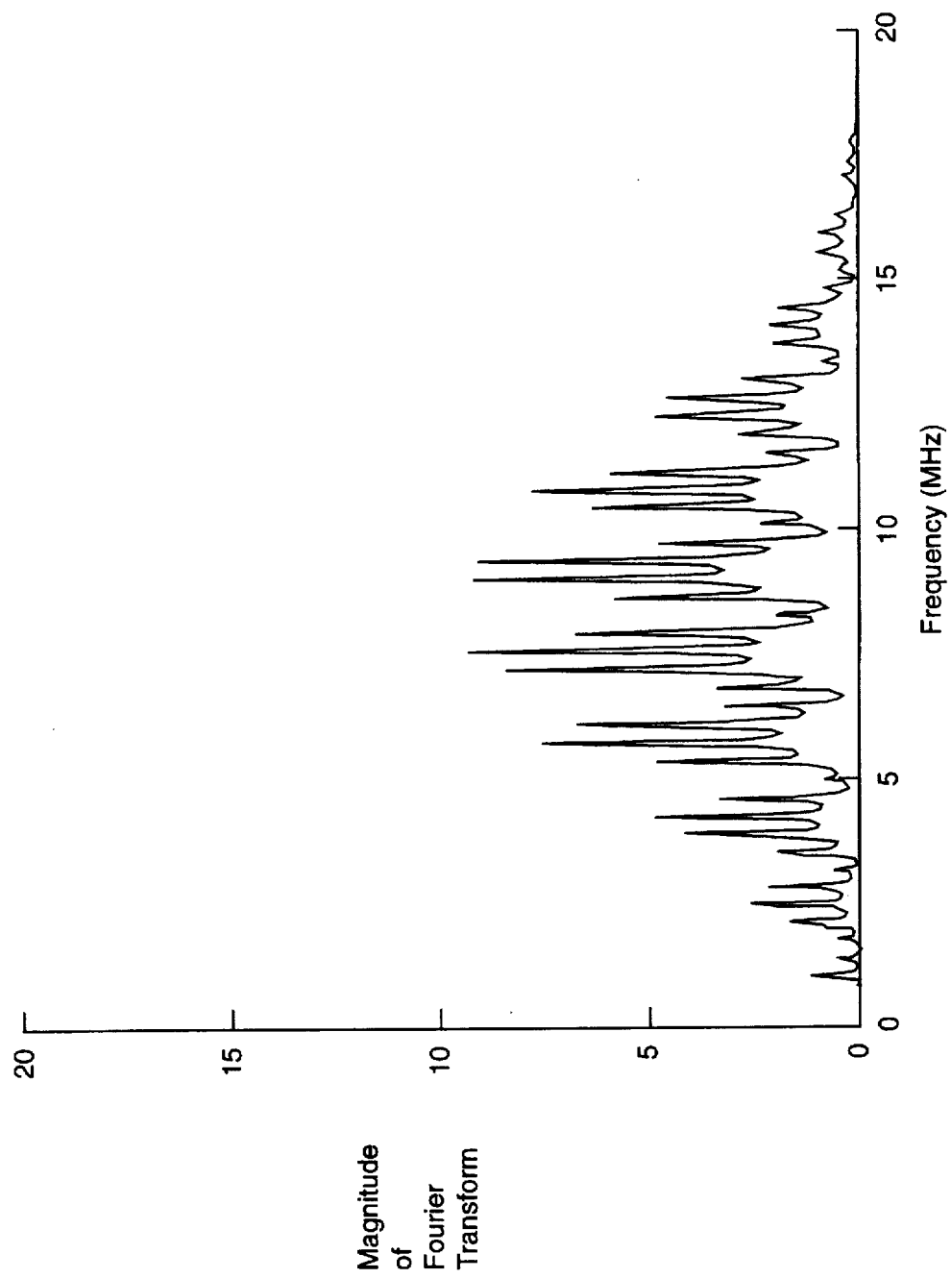
FIG. 4 is a plot of the Fourier Transform equation with arbitrary amplitude.
Figure 5:
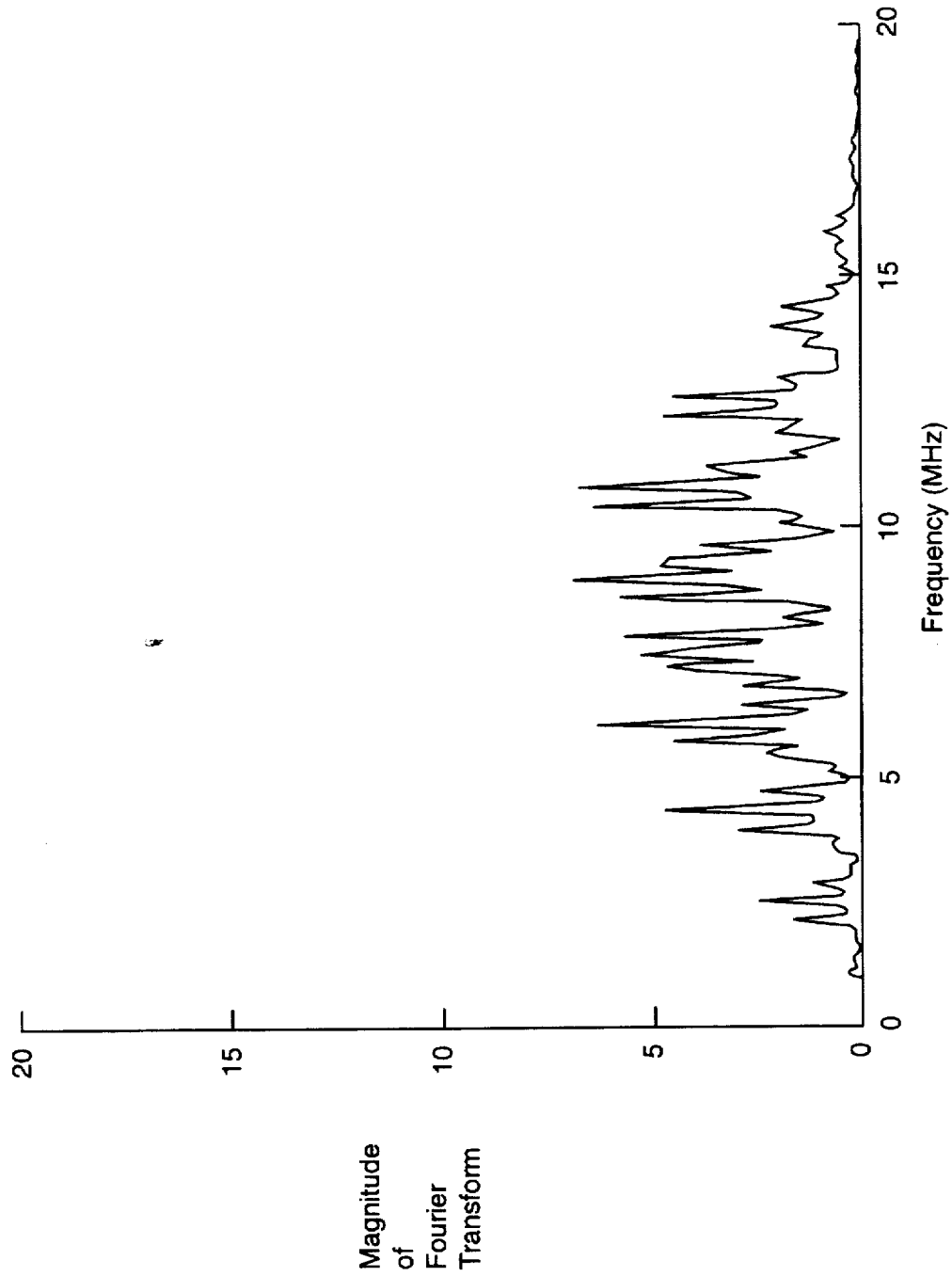
FIG. 5 is a plot of the Fourier Transform equation with discrete interpolation.

Referring more particularly to the drawings, a well-damped 10 MHz transducer one-eighth inch (⅛") diameter crystal 12 is connected to a wide band pulser-receiver 14. The pulser-receiver 14 is a sonic generator and receiver for generating, sending and receiving waves. The wide-band (non-rectified) output of the pulser-receiver 14 is connected to a digital oscilloscope 16, which has a plotter 18 connected to it to record the data output. The oscilloscope 16 provides live visual reading of the output. The data-point plotter 18 gives a graphic reading of the output. The oscilloscope 16 also has Fast Fourier Transform capability.

The transducer 12 emits an ultrasonic pulse that travels through the body 30 into the subcutaneous tissue that is under examination. This tissue reflects a sequence of small amplitude echoes back to the transducer 12. The sequence of echoes from the tissue is received by the transducer 12, which converts the ultrasonic pulse sequence into a sequence of electrical pulses. The electrical pulse sequence is amplified by the wide-band amplifier in the pulser-receiver 14 and sent to the oscilloscope 16 for measurement. The oscilloscope 16, further processes the data, displays it on a visual monitor, and sends it to a plotter 18 for a hard-copy record. The oscilloscope 16 has the ability to perform Fast Fourier Transforms on the digitized pulses 20.

Specifically, the transforming equations used are as follows:

$$G(f) = \int_{-\infty}^{\infty} h(t) e^{-i2\pi ft} dt = F[h(t)] \quad \text{1(a)}$$

-continued $$h(t) = \int_{-\infty}^{\infty} G(f)e^{i2\pi f t} dt = F[G(f)] \quad (1b)$$

where G(f) is the Fourier Transform of h(t).

The following properties of this type of transform are used:

$$F[h(t - t_0)] = \exp(-i2\pi f t_0) F[h(t)] \quad \text{(shift operation)} \quad (2a)$$

$$F\left[ \sum_{m=1}^{n} h_m(t) \right] = \sum_{m=1}^{n} F[h_m(t)] \quad \text{(addition theorem)} \quad (2b)$$

$$F[h(kt)] = \frac{1}{k} G\left(\frac{f}{k}\right) \quad \text{(similarity theorem)} \quad (2c)$$

here $i = \sqrt{-1}$

Consider the echo train from an alternating stacked sequence of tissues. The following relationships are used:

$$P_{2n-1} = P_0(T_{12}T_{21})^{2(n-1)} R_{12} \exp(-2n\alpha_1 l_1 - 2(n-1)\alpha_2 l_2) \quad \text{(odd members)} \quad (3a)$$

$$P_{2n} = -P_0(T_{12}T_{21})^{2n-1} R_{12} \exp(-2n[\alpha_1 l_1 + \alpha_2 l_2]) \quad \text{(even members)} \quad (3b)$$

In examining the echos, each received echo is subscripted with an index to indicate the temporal order of reception $$h_j(t - t_0) = P_j \exp\left(-\pi \frac{|\alpha t_j|^2}{\sigma^2}\right) \cos 2\pi f_0 (\Delta t_j) \quad (4)$$

where $t_o$ marks the reception of the first echo, and $\Delta t_j$ is the time interval between the jth received reflection and the first echo.

By allowing $G_j(f) = F[h_j(t-t_0)]$ and using (1a), (2a) and (3a) the following relationship is obtained $$G(f) = \sum_{j=1,3,5...}^{m} G_j(f) = \sum_{j=2,4,6...}^{m} F[h_j(t-t_j)] = \kappa(f) F[h_0(t)]$$

where $\kappa(f) = \sum_{j=1}^{m} (T_{12}T_{21})^{j-1} R_{12} \exp\left(-([j+1]\alpha_1 l_1 - [j-1]\alpha_2 l_2) - \right.$ (6)

$$i2\pi f \left([j+1]\frac{l_1}{c_1} - [j-1]\frac{l_2}{c_2}\right) \Big) -$$

$$\sum_{j=1}^{m} (T_{12}T_{21})^{j-1} R_{12} \exp\left(-j[\alpha_1 l_1 + \alpha_2 l_2] - i2\pi f j \left[\frac{l_1}{c_1} + \frac{l_2}{c_2}\right]\right)$$

It is assumed that the later reflections are small and equation (6) is not greatly affected by letting m approach infinity, the equation is rewritten:

$$\kappa(f) = \frac{R_{12}\exp\left[-2\alpha_1 l_1 - i4\pi f \frac{l_1}{c_1}\right] \left[1 - (T_{12}T_{21})\exp\left[-2\alpha_2 l_2 - i4\pi f \frac{l_2}{c_2}\right]\right]}{\left[1 - (T_{12}T_{21})^2 \exp\left[-2[\alpha_1 l_1 + \alpha_2 l_2] - i4\pi f \left(\frac{l_1}{c_1} + \frac{l_2}{c_2}\right)\right]\right]} \quad (7)$$

by substituting the sum for each series.

In general, any part of the transform may be used to express a relationship among the ultrasonic variables and, hence, give useful information about the significant tissue classifications. For purposes of illustration, the magnitude is used, although the real part, the imaginary part, the phase or any combination is just as instructive.

Next, the Fourier transform of the incident ultrasonic pulse, $$P = P_0 \exp\left(-\pi \frac{t_0^2}{\sigma^2}\right) \cos 2\pi f_0 t_0$$

is evaluated by substitution into equation 1(a)

$$F[h_0(t)] = \int_{-\infty}^{\infty} P_0 \exp\left(-\pi \frac{t_0^2}{\sigma^2}\right) \cos(2\pi f_0 t) dt \quad (8)$$

which upon evaluation gives $$F[h_0(t)] = \frac{P_0 \sigma \exp(-\pi \sigma^2 (f-f_0)^2)}{2} \quad f > 0 \quad (9)$$

Using standard algebraic techniques and trigonometric substitutions the magnitude is rewritten:

$$|G(f > 0, t_0 = 0)| = \frac{P_0 \sigma \exp(-\pi \sigma^2 (f-f_0)^2)}{2} \times \quad (10)$$

$$R_{12}\exp - 2H_1 \sqrt{\frac{1 - 2T\cos(4\pi f t_2)\exp(-2H_2) + (T\exp(-2H_2))^2}{1 - 2T^2\cos(4\pi f t_s)\exp(-2H_0) + (T^2\exp(-2H_0))^2}}$$

where $f_0$ is the center frequency of the ultrasonic transducer, $H_0$ is $\alpha_1 l_1 + \alpha_2 l_2$, $H_1$ is $\alpha_1 l_1$, $H_2$ is $\alpha_2 l_2$, $T$ is $(T_{12}T_{21})$, $t_2$ is $l_2/c_2$, $t_s$ is $1 \cdot l_1/c_1 + l_2/c_2$, $\alpha_1$ is the attenuation coefficient of the type 1 material, and $\alpha_2$ is the attenuation coefficient of the type 2 material.

An analysis of equation (10) shows the shape of $|G(f>0, t=0)|$ is determined by two different undulations. The more rapid undulation occurs between much smaller frequency intervals, and is determined by the cosine function in the denominator of the radical. The cosine function, $\cos 4\pi ft_s$, causes this denominator to vary between the values $$[1-(T^2 \exp(-2H_0))]^2, \text{ and } [1+(T^2 \exp(-2H_2))]^2$$

both values are perfect squares. This occurs when $\cos 4\pi ft_s$ varies between +1 and +1, for which $4\pi ft_s = n\pi$ or $$\Delta f_s = \frac{1}{4\left[\frac{l_1}{c_1} + \frac{l_2}{c_2}\right]} \quad (11)$$

where $\Delta f_s$ is the smaller frequency interval for the more rapid undulation. The numerator inside the radical also varies between $$[1-(T \exp(-2H_2))]^2, \text{ and } [1+(T \exp(-2H_1))]^2$$

but with a frequency of $$\Delta f_2 = \frac{1}{4\frac{l_2}{c_2}} \quad (12)$$

where $\Delta f_s$ is the frequency of the slower undulation. Solving equations (11) and (12) for $l_1$ and $l_2$ respectively it is determined:

$$l_1 = \frac{c_1}{4\Delta f_s}\left[1 - \frac{\Delta f_s}{\Delta f_2}\right] \quad (13a)$$

$$l_2 = \frac{c_2}{4\Delta f_2} \quad (13b)$$

By measuring the frequency intervals, $\Delta f_s$ and $\Delta f_2$, one can determine an average thickness 22 of a ground substance, $l_2$ and the cluster of substantive cells, $l_1$.

The plot of equation (10) reveals a series of maximum and minimum values. One can trace the envelopes of the relative maxima and minima by noting the occurrence when cos $4\pi f t_s = +1$ and $-1$, respectively $$|G_{upper}(f > 0, t_0 = 0)| = \frac{A\sigma\exp(-\pi\sigma^2(f-f_0)^2)}{2} \times \quad (14)$$

$$R_{12}\exp(-2H_1)\frac{\sqrt{1 - 2T\exp(-2H_2)\cos 4\pi f t_2 + (T\exp(-2H_2))^2}}{1 - T^2\exp(-2H_0)}$$

while $$|G_{lower}(f > 0, t_0 = 0)| = \frac{A\sigma\exp(-\pi\sigma^2(f-f_0)^2)}{2} \times \quad (15)$$

$$R_{12}\exp(-2H_1)\frac{\sqrt{1 - 2T\exp(-2H_2)\cos 4\pi f t_2 + (T\exp(-2H_2))^2}}{1 + T^2\exp(-2H_0)}$$

For a given frequency, $f_1$ (e.g. at a maximum for $|G_{upper}(f_1, t=0)|$) the ratio, $$\epsilon = \frac{|G_{upper}(f_1, t_0 = 0)|}{|G_{lower}(f_1, t_0 = 0)|} = \frac{1 + T^2\exp(-2H_0)}{1 - T^2\exp(-2H_0)} \quad (16)$$

Solving for $T^2$ gives $$T^2 = 1 - R_{12}^2 = \left(\frac{\epsilon - 1}{\epsilon + 1}\right)\exp(2H_0) \quad (17)$$

where $\epsilon$ is the ratio of maximum envelope to minimum envelope. Using data measurements one can obtain the values of $\epsilon$ as a function of frequency and by curve fitting obtain values for T and $H_0$.

In determining the collagen content in the ground substance, equation (17) is solved for and $$R_{12} = \frac{Z_1 - Z_2}{Z_1 + Z_2}, R_{12} = -R_{21}$$

is used to obtain $$Z_2 = Z_1 \left[\frac{1 - \sqrt{1 - \left(\frac{\epsilon-1}{\epsilon+1}\right)\exp(2H_0)}}{1 + \sqrt{1 - \frac{\epsilon-1}{\epsilon+1}\exp(2H_0)}}\right] \quad (18)$$

where $Z_1$ is the acoustic impedance of the cluster of fat cells, which is assumed to be the same as the acoustic impedance of the lipids stored in the fat cell clusters. These lipids possess a measurable acoustic impedance. Combined with the experimental determination of $\epsilon$, $Z_1$ and $H_0$, $Z_2$, the acoustic impedance of the ground substance, can be calculated. This analysis suggests a closer examination of the factors of the ground substance's acoustic impedance.

In determining the collagen and mass density [gms/cm] of tissues, the published values of the mass density of pure collagen varies from 1.16 to 1.33. However, collagen is only one of the many specialized molecular species found in tissues. Upon examination of the mass densities of the other constituents however it was discovered that a reasonable mass density model for ultrasonic applications is essentially a two-component mixture comprised of collagenous and other materials. Using the definition of mass density and further assuming that the collagen fiber diameters are smaller than the ultrasonic wavelength in the tissue it can be written $$\rho = \frac{1}{1 - \frac{C}{100} + \frac{C}{100}} \quad (19)$$
$$\qquad \frac{\rho_1}{\rho_1} + \frac{\rho_2}{\rho_2}$$

where C is the wet weight percent of collagen, $\rho_1$ is the density of the non-collagenous material in the tissue and $\rho_2$ is the density of the collagenous material.

The sound velocity in a mouse tail tendon fibers has been reported to be $1.733 + 0.056 \times 10^5$ cm/sec (Goss and O'Brien, Journal of Acoustical Society of America, Vol. 65, pages 507–511; 1979). Tendon collagen is 30% wet weight. O'Brien (in "Proceedings Ultrasonic International 77", IPC Science and Technology Press, Guildford, England, pages 194–205; 1977) has empirically determined that the velocity of sound in tissue, c, depends upon the percent wet weight of collagen in the tissue's composition, C, according to the following relation $$c = (1.588 + 0.032 \log_e C) \times 10^5 \text{ cm/sec} \quad (20)$$

The acoustic impedances are calculated to be $$Z_2 = \frac{(1.588 + 0.032 \log_e C) \times 10^5}{1 - \frac{C}{100} + \frac{C}{100}} \text{ gms/cm}^2\text{sec} \quad (21)$$
$$\qquad \frac{\rho_1}{\rho_1} + \frac{\rho_2}{\rho_2}$$

The measurement and analysis technique gives $Z_2$ 26. With equation (21) it is possible to determine the weight percent of collagen in the ground substance in-vivo if the density is known of the collagen fibers. But the density of collagen fibers depends in part on the health and nutrition of the patient. This makes the value of $Z_2$ a potentially good indicator of tissue health with the larger values of $Z_2$ indicating more and better grade collagen in the ground substance. By assuming a reasonable range of values for the collagen fiber density the determination gives a range of values for the weight percent of collagen in tissues in-vivo 28. The linkage is the degradation of the mechanical properties of these tissues is directly involved with the failure of the tissue's mechanical properties. That connection is the weight percent of collagen and the collagen's density (the higher the density, the better its structural properties) in the ground substance.

Using a curve fitting algorithm for the experimentally determined quantity $$\left(\frac{\epsilon - 1}{\epsilon + 1}\right) \quad (22)$$

Both $T_2$ and $H_0$ can be determined by solving the equation $$T^2\exp(-2H_0) = \left(\frac{\epsilon - 1}{\epsilon + 1}\right) \quad (23)$$

where H is $\alpha_1 l_1 + \alpha_2 l_2$. Since $l_1$ and $l_2$ are determined according to equations 13(a), 13(b) and $\alpha_1$ can be estimated from scattering and absorption of ultrasonic waves by fat cells, one can determine $\alpha_2$ $$\alpha_2 = \frac{H_0 - \alpha_1 l_1}{l_2} \quad (24)$$

which can be measured as a function of frequency. This information can be used to assess the quality of collagen fibers and the areal density of the fiber network (weave) in the ground substance. A correlation with invasive measurements and to a lesser extent to in vitro measurements will permit the best estimates of these quantities.

In this manner, it is clear that more than a broad classification of healthy or unhealthy can be realized for smaller regions of interest. Most significantly, a diagnosis for the development of pressure ulcers can be facilitated through the use of this invention.

It is specifically intended that the present invention not be specifically limited to the embodiments and illustrations contained herein, but embrace all such modified forms thereof as come within the scope of the following claims.

What is claimed is:

1. A method for detecting histological properties of human tissue, composed of an iterated stacking sequence of cellular material and collagen containing structural components, using data obtained from ultrasonic ray inputs, comprising the steps of:

emitting a high-frequency ultrasonic pulse into human tissue;

collecting a subsequent sequence of reflected echoes from said tissue;

converting said echoes into a sequence of electrical pulses;

amplifying said sequence of electrical pulses;

performing a Fourier transform upon a time record of said sequence of electrical pulses;

selecting any part of said transform;

plotting a display of said transform in terms of said part;

evaluating said display to quantitatively determine an index of relative collagen content in said collagen containing structural component, wherein said evaluating is comprised of:

calculating an average thickness of said cellular material and collagen containing components;

determining a ratio for a series of maximum and minimum values that comprise said display and;

calculating an acoustic impedance value for said collagen containing structural component.

2. The method as in claim 1 wherein said evaluating includes calculating an attenuation coefficient for said collagen containing structural component.

3. Apparatus for classifying histological properties of human tissue comprising:

means for generating ultrasound pulses into human tissue;

transducer means for applying said ultrasound pulses to said tissue and receiving returned ultrasound from said tissue body;

means for converting said returned ultrasound pulses into a sequence of electrical pulses;

means for amplifying said pulses;

means for performing Fast Fourier Transforms on said amplified pulses;

means for selecting any part of said transform;

means for plotting a display of said transform in terms of said part;

means for evaluating said display to quantitatively determine an index of collagen content in said tissue, wherein said means for evaluating said display is a means for calculating an average thickness of said cellular material and collagen containing components;

determining a ratio for a series of maximum and minimum values that comprise said display, and;

calculating an acoustic impedance value for said collagen containing structural component.

4. The apparatus of claim 3 wherein said means for evaluating said display is a means for calculating an attenuation coefficient for said collagen containing structural component.

\* \* \* \* \*